United States Patent
Heidenreich et al.

(10) Patent No.: US 10,191,130 B2
(45) Date of Patent: Jan. 29, 2019

(54) DEVICE FOR SEQUENTIAL EXAMINATION OF A MEASUREMENT OBJECT BY MEANS OF MPI AND MRI METHODS

(71) Applicant: BRUKER BIOSPIN MRI GMBH, Ettlingen (DE)

(72) Inventors: Michael Heidenreich, Karlsruhe (DE); Jochen Franke, Karlsruhe (DE); Volker Niemann, Ispringen (DE); Rainer Pietig, Malsch (DE)

(73) Assignee: BRUKER BIOSPIN MRI GMBH, Ettlingen (DE)

( * ) Notice: Subject to any disclaimer, the term of this patent is extended or adjusted under 35 U.S.C. 154(b) by 751 days.

(21) Appl. No.: 14/647,452

(22) PCT Filed: Nov. 22, 2013

(86) PCT No.: PCT/EP2013/074467
§ 371 (c)(1),
(2) Date: May 27, 2015

(87) PCT Pub. No.: WO2014/082927
PCT Pub. Date: Jun. 5, 2014

(65) Prior Publication Data
US 2015/0316628 A1    Nov. 5, 2015

(30) Foreign Application Priority Data

Nov. 29, 2012   (DE) .................. 10 2012 221 838

(51) Int. Cl.
*G01R 33/385*  (2006.01)
*A61B 5/05*    (2006.01)
(Continued)

(52) U.S. Cl.
CPC .......... *G01R 33/385* (2013.01); *A61B 5/0035* (2013.01); *A61B 5/0515* (2013.01);
(Continued)

(58) Field of Classification Search
CPC .. G01R 33/385; G01R 33/3856; A61B 5/0515
(Continued)

(56) References Cited

U.S. PATENT DOCUMENTS

| 2003/0065703 | A1 | 5/2003 | Gleich |
| 2009/0234219 | A1* | 9/2009 | Kruip .................. A61N 5/1049 600/411 |

(Continued)

FOREIGN PATENT DOCUMENTS

JP    2009-195614    9/2009

OTHER PUBLICATIONS

Gleich, Bernhard et al., "Tomographic imaging using the nonlinear response of magnetic particles". Nature, vol. 435/30, Jun. 2005.
(Continued)

*Primary Examiner* — Amy He
(74) *Attorney, Agent, or Firm* — Paul Vincent (57) ABSTRACT

A device for alternating examination of a measurement object (170) by means of MPI and MRI with two magnetic field-generating elements is presented. The device is characterized by a main magnet coil system with two coaxial partial coil systems (100$a1$, 100$a2$; 100$b2$, 100$b1$) arranged mirror-symmetrically relative to a central plane running perpendicularly to the z-axis through the first volume under investigation (162). The volumes under investigation are superimposed. A polarity reversal device (190) reverses the polarity of the current through a partial coil system and the main magnet coil system generates a homogeneous magnetic field of at least sixth order in the first volume under investigation when the partial coil systems have identical polarity, and a spatially strongly varying magnetic field profile in the second volume under investigation when the polarities are opposite. Repositioning of the measurement object is thereby simplified or can even be eliminated.

13 Claims, 11 Drawing Sheets

(51) Int. Cl.
*G01R 33/48* (2006.01)
*A61B 5/00* (2006.01)
*G01R 33/38* (2006.01)

(52) U.S. Cl.
CPC ..... *G01R 33/3856* (2013.01); *G01R 33/4808* (2013.01); *G01R 33/3804* (2013.01)

(58) Field of Classification Search
USPC .................................................. 324/309, 318
See application file for complete search history.

(56) References Cited

U.S. PATENT DOCUMENTS

| | | |
|---|---|---|
| 2010/0033173 A1 | 2/2010 | Gleich |
| 2010/0052668 A1 | 4/2010 | Gleich |
| 2011/0050229 A1 | 3/2011 | Chan |
| 2011/0098558 A1* | 4/2011 | Weaver .................... A61B 5/05 600/420 |
| 2012/0119739 A1 | 5/2012 | Gleich |
| 2013/0303885 A1 | 11/2013 | Hoshino |

OTHER PUBLICATIONS

Sattel, Timo et al., "Single-sided device for magnetic particle imaging". J.Phys.D: Appl. Phys. 42 (2009) 02201 (5pp).

Weizenecker, J. et al., "Three-dimensional real-time in vivo magnetic particle imaging", Phys. Med. Biol. 54 (2009) L1-L10.

Weizenecker, J. et al., "A simulation study on the resolution and sensitivity of magnetic particle imaging", Phys. Med. Biol. 52 (2007) 6363-6374.

Knopp, T. et al., "Trajectory analysis for magnetic particle imaging", Phys. Med. Biol. 54 (2009) 385-397.

* cited by examiner

DEVICE FOR SEQUENTIAL EXAMINATION OF A MEASUREMENT OBJECT BY MEANS OF MPI AND MRI METHODS

This application is the national stage of PCT/EP2013/074467, filed on Nov. 22, 2013 and also claims Paris convention priority from DE 10 2012 221 838.6, filed Nov. 29, 2012, the entire disclosures of which are hereby incorporated by reference.

BACKGROUND OF THE INVENTION

The invention concerns a device for alternating examination of a measurement object by means of MPI (magnetic particle imaging) and by means of MRI (magnetic resonance imaging), comprising at least two elements that generate a magnetic field, the device having a first volume under investigation for MRI operation, in which a homogeneous field is generated, and also a second volume under investigation for MPI operation, in which a spatially strongly varying magnetic field profile is generated, the field vectors of which are different with respect to direction and/or magnitude at all spatial points and that have a field magnitude of zero at one spatial point, wherein the device comprises a resistive drive field coil system for generating a drive field, and also a resistive MRI gradient coil system.

A device of this type is disclosed by reference [3] (Weizenecker et al., 2009).

A large number of tomographic imaging methods have been invented during the last decades, such as e.g. computer tomography (CT) by Hounsfield in 1969, magnetic resonance imaging (MRI) by Lauterbur and Mansfield in 1973 or positron emission tomography (PET) by Ter-Pogossian and Phelps in 1975. Imaging methods have become more and more important in today's medical diagnostics due to continuous further development of the hardware, the sequence and/or reconstruction algorithms. The diagnostic informative value using imaging methods could be further increased through combination of individual imaging methods into so-called hybrid systems (e.g. PET-CT in clinical operation since 2001 and MRI-PET in clinical operation since 2010). All hybrid systems are based on synergetic combination and/or graphic superimposition of complementary information of the individual modalities. Thus, CT data of a PET-CT hybrid system is used e.g. for morphological information and also for attenuation correction of the PET data.

Gleich and Weizenecker invented a further tomographic imaging method in 2001 called magnetic particle imaging (MPI) (DE10151778A1). This young and rapidly developing volumetric imaging method is used for detecting the spatial distribution of applied superparamagnetic nanoparticles (SPIO). This method provides spatial resolution as well as high temporal resolution (cf. references [1-3]).

The basic principle of MPI is based on excitation of the nanoparticles by means of a temporally varying magnetic field, the so-called "drive field" (DF), with an excitation frequency $f_0$. Due to the non-linear magnetization curve of the SPIOs, the particle responses are harmonics of $f_0$, which are detected by means of receiver coils and are utilized for image reconstruction. Since tissue provides a negligibly small and non-linear response to the excitation frequency $f_0$, this method offers a large contrast due to acquisition merely of the particle response. Spatial encoding is based on the effect that particle magnetization is saturated starting from a specific magnetic field strength. Due to magnetic excitation with the frequency f0, the magnetization of the saturated SPIOs changes only minimally and these changes then do not or only hardly contribute to the particle response. In order to utilize this saturation effect, a static magnetic field gradient, the so-called "selection field (SF)", is generated with a field-free point (FFP). Departing from this FFP, the magnetic field strength increases in all spatial directions.

A magnetic field behavior of this type can e.g. be generated by permanent magnets with opposite magnetization direction or by means of a Maxwell electromagnetic coil pair. Due to the saturation effect, only particles in the direct vicinity of the FFP are excited and thus contribute to the particle response. The extension of the FFP, and therefore the sensitivity of the MPI method depends on the magnetic field strength at which the particles reach saturation and also on the gradient strength of the SF with which the magnetic field rises starting from the FFP (cf. references [4, 5]). In order to allow volumetric imaging, the FFP is controlled in relation to the object under investigation by e.g. superposition of additional magnetic fields and/or by mechanical movement of the object under investigation.

The quantitative MPI method offers promising possibilities for non-invasive applications in the field of molecular and medical imaging such as e.g. cell tracking or cancer diagnosis and also in the field of cardiovascular diagnosis and blood vessel imaging due to its high sensitivity and its high temporal resolution. In contrast to other imaging methods such as e.g. CT and MRI, the acquired current MPI image data sets still have a relatively low spatial resolution in the millimeter range. This resolution limitation is determined by the currently available nanoparticles and the magnetic field gradient that can be technically realized. The data with high sensitivity exclusively with respect to the applied nanoparticles moreover allows statements about the quantitative distribution of the nanoparticles, which includes, however, only limited morphological information. For this reason, it is extremely difficult to unambiguously allocate the measured particle distribution to its morphological location of generation.

Other volumetric imaging methods, such as e.g. the MRI method that has been clinically used for a long time, are ideally suited for detecting high-resolution morphological information. MRI technology is based on a strong homogeneous magnetic field, the so-called polarization field (PF), and also on alternating electromagnetic fields in the radio frequency range which are used for resonantly exciting specific nuclei of the object under investigation (cf. reference [6]). The excited nuclei emit, in turn, alternating electromagnetic fields that induce electric signals in the receiver coil. When several magnetic field gradients are used, the signal is spatially encoded and can be reconstructed by means of suitable algorithms. MRI not only allows acquisition of anatomical information with high spatial resolution with diverse soft tissue contrasts but also offers further differentiated techniques that permit access to many physiological parameters such as e.g. water diffusion or permeability [6]. In MR spectroscopic imaging, it is additionally possible to spatially present metabolic and biochemical processes. In contrast to MPI, the MRI technique is a relatively insensitive and slow imaging method with acquisition times in the range of seconds to minutes.

Due to the unique properties of both volumetric imaging modalities, MPI and MRI are largely complementary with respect to their information content. A combination of both methods and synergetic utilization of their properties, the high sensitivity and also temporal resolution of the MPI technology and the diverse soft tissue contrasts and thus excellent morphological information of MRI technology, enables superior diagnostic informative value. A superposition/fusion of both complementary image data sets has been realized up to now only by means of two separate and independent modalities of MPI and MRI (cf. reference [3]) due to the global lack of availability of an integral device (hybrid device) combining these two modalities at the present time.

However, the use of two separate modalities involves some difficulties, i.a. the co-registration of both data sets with different reference coordinates. The co-registration is aggravated by shifting and deformation, which generally cannot be avoided due to relocation or transport of the object under investigation from the one modality to the other. The intermodality transport moreover prevents direct correlation of the two data sets in time. There are further logistical problems e.g. in case of studies on small animals, which require continuous anaesthetization of the test animal. The provision of two stand-alone modalities also results in high cost and extensive space requirements.

These difficulties were partially addressed in the earlier German patent application DE 10 2012 216 357.3, which was not published before the filing date of the present application. It describes an integrally structured hybrid system, in which the main magnet coil system has at least one element that generates a magnetic field and also generates a magnetic field portion both in the MRI volume under investigation and also in the MPI volume under investigation that is indispensable for both volumes under investigation. Such an integrally structured hybrid system generates a magnetic field behavior that suits both the requirements for MRI and also MPI modalities, wherein the spatial points of the centers of the two volumes under investigation do not coincide and the two volumes under investigation are not superimposed on each other. Due to these features, relocation of the measurement object is absolutely necessary, which aggravates co-registration of both data sets. Relocation also limits the chronological succession of both investigations.

US 2012/0119739 A1 also addresses a combination of MPI and MRI and the problems arising thereby, in particular, that the two measurement methods require coils for generating the magnetic field, which have clearly different geometries. These difficulties shall be solved by using pre-polarized MRI in accordance with the teaching of US 2012/0119739 A1.

In contrast thereto, it is the underlying purpose of the present invention to improve a device of the type described above in an inexpensive fashion with as simple technical means as possible in such a fashion that the above-described difficulties of a switchable combination of both modalities in an integrally structured hybrid device can be reduced or eliminated, thereby simplifying or even eliminating the need for relocation of the measurement object.

SUMMARY OF THE INVENTION

This object is achieved by a device in accordance with the independent claim, which is characterized in that the device comprises a main magnet coil system that is arranged around a z axis and comprises two coaxial partial coil systems that are arranged mirror-symmetrically with respect to a central plane running perpendicularly to the z axis through the first volume under investigation, the first and the second volume under investigation are at least partially superimposed such that a polarity reversal device for reversing the polarity of the current through one of the partial coil systems is provided and the main magnet coil system is designed in such a fashion that it generates a homogeneous magnetic field of at least 6th order in the first volume under investigation when the polarities of the partial coil systems are the same and generates a spatially strongly varying magnetic field profile in the second volume under investigation when the polarities are opposite.

The present invention proposes possible magnet system configurations that meet both the requirements for MRI and also MPI imaging. The two overlapping areas of investigation permit optimum utilization of the measurement volume available.

The present invention offers numerous advantages and considerably improves operation in comparison with prior art and also yields significantly more detailed data about the measurement object:

a. recording of morphological reference image data sets by means of MRI is rendered possible.

b. the high base magnetic field homogeneity of the main magnet coil system permits utilization of MRI pulse programs that are sensitive with respect to homogeneity.

c. configuration with reversible polarity:
 i. relocation is not necessary
 ii. repositioning is not necessary
 iii. no expenses for logistics/anaesthetization can be continued without interruption
 iv. quick change between the two modalities can be realized
 v. both modalities may have the same magnetic center
 vi. the same coordinate system
   1. simple image fusion
   2. simple detection of the desired "field of view" (FoV) by means of MRI.

d. increase of the clinical informative value by the two methods//complementary information//sum of combination of both modalities is larger than the sum of the two individual modalities e. MPI: high sensitivity//permits molecular imaging f. MRI: high morphological information//large selection of dedicated acquisition protocols.

For an integrally structured hybrid device consisting of MRI and MPI modalities, the magnet system configuration must generate a magnetic field behavior that includes both a homogeneous field area for MR imaging and also a field area with a spatial field gradient including a field zero crossing. The field region that contains the field magnitude zero is called "field-free point" (FFP) in MPI technology.

Further variants of the invention and advantageous properties and designs are described in the dependent claims in the form of embodiments and further developments of the invention.

Superconducting electromagnetic coil systems, resistive electromagnetic coil systems, permanent-magnetic systems and/or a combination therefrom may be used for generating magnetic fields.

One class of embodiments that is preferred for the practical use of the inventive device is characterized in that the magnet system comprises a superconducting electromagnetic coil system that is arranged within a cryostat. The configuration is to be realized in connection with one single cryostat. Superconducting electromagnets permit generation of a high basic magnetic field $B_0$ and of a strong magnetic field gradient G.

In a further class of embodiments, the magnet system may alternatively or supplementarily be designed as a resistive electromagnetic coil system, in which all available partial coils are electrically connected in series. One design of the field generator by means of a resistive electromagnetic coil system, in which all partial coils are connected in series and are coaxially arranged, can be freely selected within defined limits by presetting the coil current, the height of the basic magnetic field and the strength of the magnetic field gradient. This is particularly interesting for the MPI mode since expansion of the Fovs with constant DF amplitude is proportional to 1/G. Resistive electromagnetic coil systems moreover permit quick switching off of the base field/gradient field when the system is not in use, which minimizes the risks that accompany strong magnetic fields. Switching off the base magnetic field moreover permits optimum utilization of new approaches of system calibration by means of the "System Calibration Unit" in MPI imaging (cf. reference [7]).

In particularly preferred embodiments of the inventive device, the main magnet coil system is optimized in view of minimum power loss for a specific field strength by means of a dispersed current density distribution. These embodiments are characterized by reduced energy consumption, the possibility of realizing relatively high field strengths (in the present case approximately 0.5 T) by means of a resistive main magnet coil system and by reduced requirements for a cooling apparatus.

A further class of advantageous embodiments of the invention is characterized in that at least one of the partial coil systems is designed as a solenoid coil or a normal configuration of solenoid-shaped components.

In further embodiments of the inventive device, the polarity reversal device for reversing the polarity of the current is integrated in a power supply unit for the main magnet coil system by means of a partial coil system. This provides an advantageous safety concept in which reversal of the polarity is only permitted when the current in the main magnet coil system is zero. The inverter of the device for reversing the polarity can be electrically controlled. Reversal of polarity can be controlled via software or by a pulse program. This also permits particularly precise reversal of polarity and also fast inter-modality change.

In order to minimize interferences/disturbances between the MRI partial components and the MPI partial components, the volumes under investigation should be shielded with respect to RF (radio frequency) radiation and LF (low frequency) radiation.

In preferred embodiments of the inventive device, the resistive drive field coil system is manufactured from an RF ("radio frequency") strand. The large number of fine, mutually insulated and interwoven individual wires of the RF strand increases the cross-section that is effectively involved in the current flow. The RF strand moreover generates small conduction loss at high frequencies in contrast to a solid wire, since solid wire is limited e.g. by the skin effect and proximity effect. For this reason, a drive field of high quality can be realized.

In further advantageous embodiments of the invention, the electric feed lines of the resistive drive field coil system are designed as quadrupoles for reducing the stray field based on the feed lines and the sensitivity with respect to coupling-in of stray fields.

In particularly preferred embodiments of the inventive device, the resistive drive field coil system has an active cooling system that circulates an electrically non-conductive coolant through the drive field coil system within electrically non-conductive channels of the cooling system. Active cooling permits enlargement of the respective working area of the components without destroying the assembly. Generation of eddy currents induced by the MRI gradient and the drive field itself is moreover decisively reduced since the coolant and, in particular, the channels of the cooling system are electrically non-conductive.

Other advantageous embodiments of the invention are characterized in that the electrical feed lines of the resistive drive field coil system are laid within feed or discharge lines for coolant of the cooling system. This optimizes cooling of the connecting lines and reduces the cost by reducing the required RF strand in contrast to passively cooled DF feed lines.

In further preferred embodiments of the inventive device, the MRI gradient coil system is produced from RF strand. This is advantageous i.a. for the following reasons:
   a. transparency for LF radiation of the drive field
   b. minimizing the generated eddy currents within the MRI gradient
     i. induced by the drive field
       1. minimizing attenuation of the drive field amplitude
     ii. induced by the MRI gradient itself
       1. possibility of realizing steep/fast switching flanks
       2. reducing artefacts generated by eddy currents.

Embodiments of the inventive device, which are characterized in that the MRI gradient coil system has an active cooling system that circulates an electrically non-conductive coolant within the MRI gradient coil system in electrically non-conductive channels of the cooling system have i.a. the following advantages:
   a. The respective working area of the components can be enlarged by active cooling without destroying the assembly.
   b. Transparency of the drive field for RF radiation is obtained.
   c. The eddy currents generated within the MRI gradients can be minimized:
     i. eddy currents induced by the drive field:
       1. minimizing the attenuation of the drive field amplitude
       2. possibility of realizing precise DF trajectories
     ii. eddy currents induced by the MRI gradient itself:
       1. possibility of realizing steep/fast switching flanks
       2. reducing artefacts generated by eddy currents
       3. possibility of realizing precise gradient trajectories.

In other likewise advantageous embodiments of the invention, the MRI gradient coil system is actively and/or passively shielded. This results in minimization of the generated eddy currents outside of the MRI gradient and therefore of steep/fast switching flanks and of precise gradient trajectories and in reduction of artefacts that are generated by eddy currents.

There are also particularly preferred embodiments of the inventive device, which are characterized in that all field-generating elements for MRI and MPI have the same magnetic center. This has i.a. the following advantages:
   a. the same magnetic center of all field-generating elements (exclusive of MRI RF TxRx coil)
   b. the same coordinate system
     i. simple image fusion
     ii. simple detection of the desired "field of view" (FoV) by means of MRI
   c. Relocation/repositioning is not required.

Further advantages of the invention can be extracted from the description and the drawings. The features mentioned above and below may be used in accordance with the invention either individually or collectively in arbitrary combination. The embodiments shown and described are not to be understood as an exhaustive enumeration, rather have exemplary character for describing the invention. The invention is illustrated in the drawing and is explained in more detail with reference to embodiments.

DESCRIPTION OF THE PREFERRED EMBODIMENT

Figure 1:
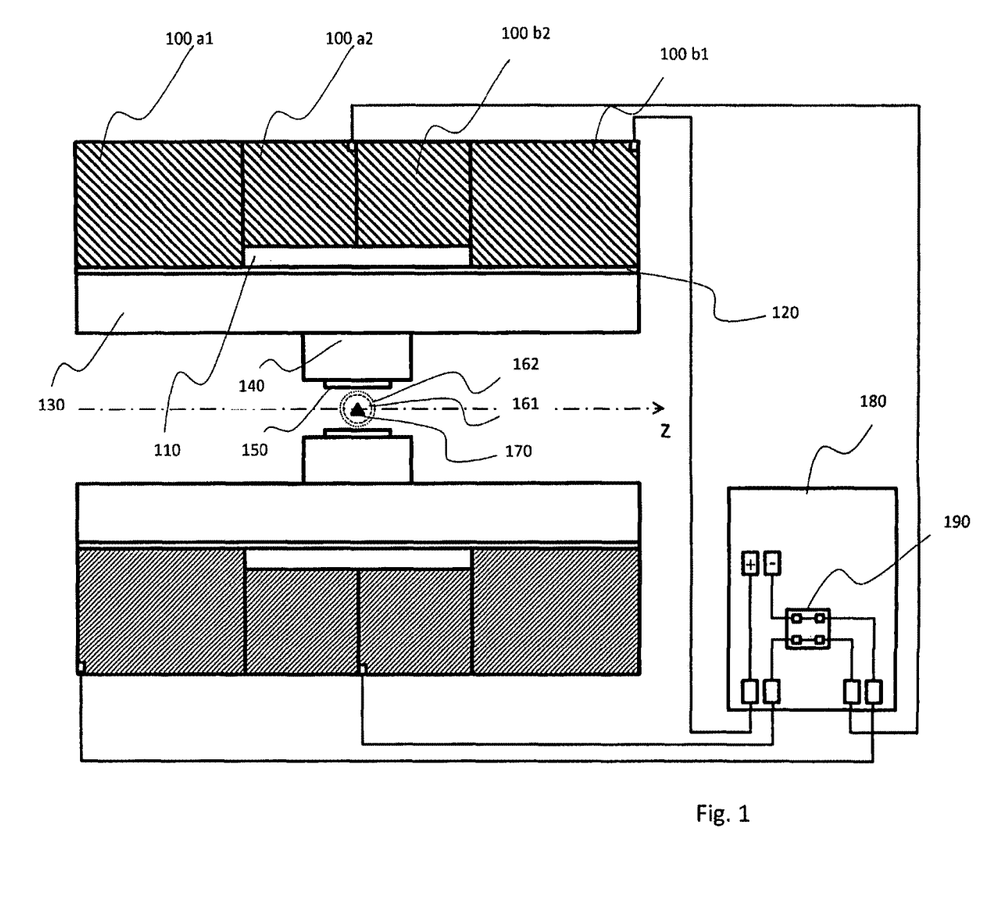
FIG. 1 shows a schematic longitudinal section through the main magnet coil system of the illustrated embodiment in the MRI mode (polarization field). The dark hatching represents a current flow of the main magnet coil system 100a1, 100a2, 100b1, 100b2 out of the image plane, the light hatching represents a current flow into the image plane. Both partial coil systems 100a1-2 and 100b1-2 are connected in series and with the same polarity to the power supply unit 180. Illustrated are also the shim coil system 110, a copper tube as passive shielding 120 of the drive field, the MRI gradient coil system 130, the drive field coil system 140 and the MRI Tx/Rx RF coil system 150. The object under investigation 170 and the volumes under investigation 161, 162 are indicated.
Figure 2:
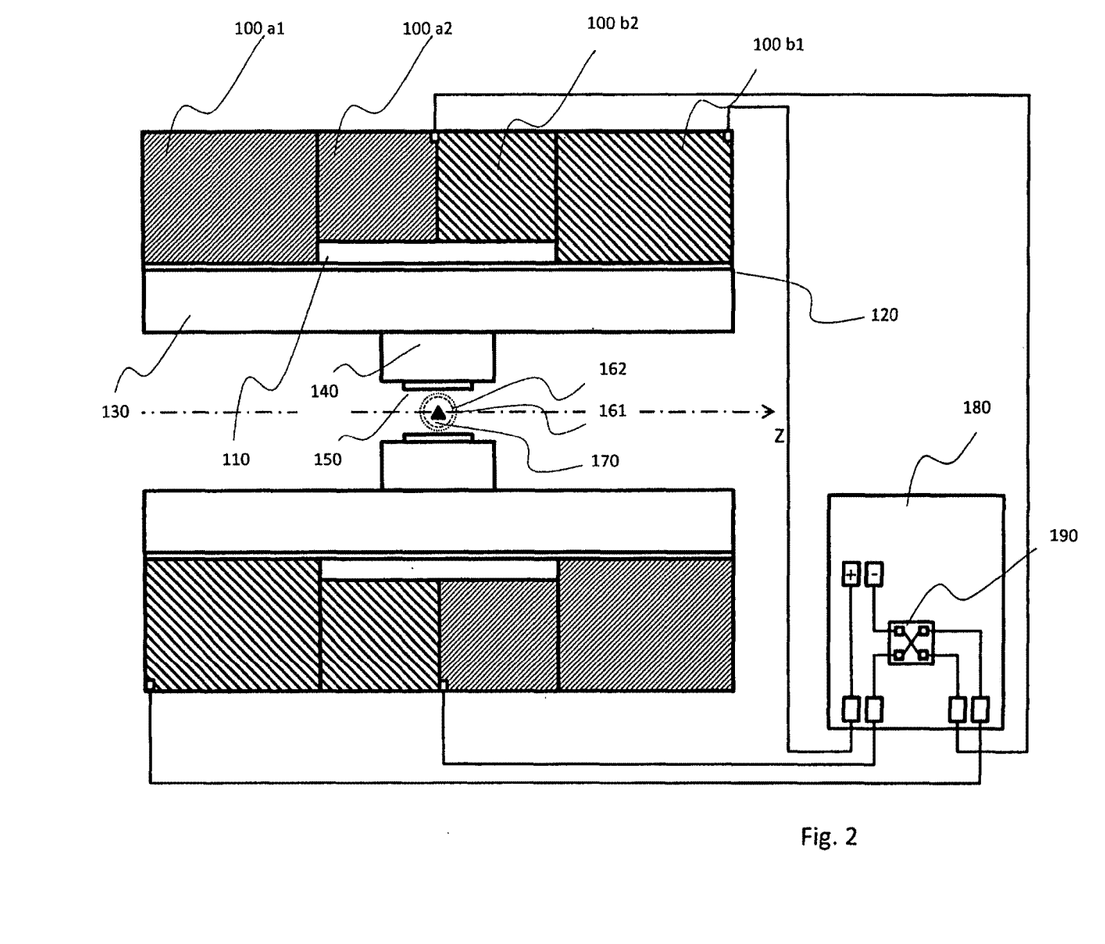
FIG. 2 shows the longitudinal section of FIG. 1 in the MPI mode (selection field). The dark hatching represents a current flow of the main magnet coil system 100a1, 100a2, 100b1, 100b2 out of the image plane, the light hatching represents a current flow into the image plane. Both partial coil systems 100a1-2 and 100b1-2 are connected in series to the power supply unit 180, however, with opposite polarity by actuating the device for reversing the polarity 190.

The embodiment illustrated in FIGS. 1 and 2 shows an integral structure of an MPI-MRI hybrid system that is suited e.g. for studies on small animals and contains all partial components described in the claims and enables alternating/sequential investigation by means of MPI and MRI without relocating the measurement object 170. The integral structure enables utilization of partial components such as e.g. main magnet coil system, control software, data acquisition components, current or voltage sources, safety monitoring for safe operation of the hybrid system, cooling unit as well as laboratory infrastructure for both operating modes (MPI and MRI).

In this embodiment, the main magnet coil system is realized by two coaxially arranged solenoid-shaped partial coil systems 100a1, 100a2; 100b1, 100b2, which are arranged mirror-symmetrically with respect to a central plane that is perpendicular to the z axis. Each of these resistive partial coil systems is realized by hollow copper conductors, edge length 10 mm×10 mm, bore diameter 4 mm, which are electrically connected in series and are connected in parallel with respect to cooling.

The structural form of the main magnet coil system is optimized with respect to maximum power loss of 61 kW for a magnetic field of 6th order of a strength of 0.5 T in the volume under investigation 162 by means of dispersed current density distribution. This means that the current density in this structural form is distributed both axially and also radially in a uniform fashion over the overall area of the coil. This results in an overall length of 820 mm, an outer diameter of 600 mm, an inner diameter of 328 mm and a copper weight of approximately 1000 kg, wherein the partial coil systems a and b each consist of two partial coil system units 100a1, 100a2 and 100b1, 100b2, which contain 22 or 14 coaxially arranged hollow copper conductor elements with 12 or 10 radial windings. A coolant flows through the hollow copper conductors.

Figure 4:
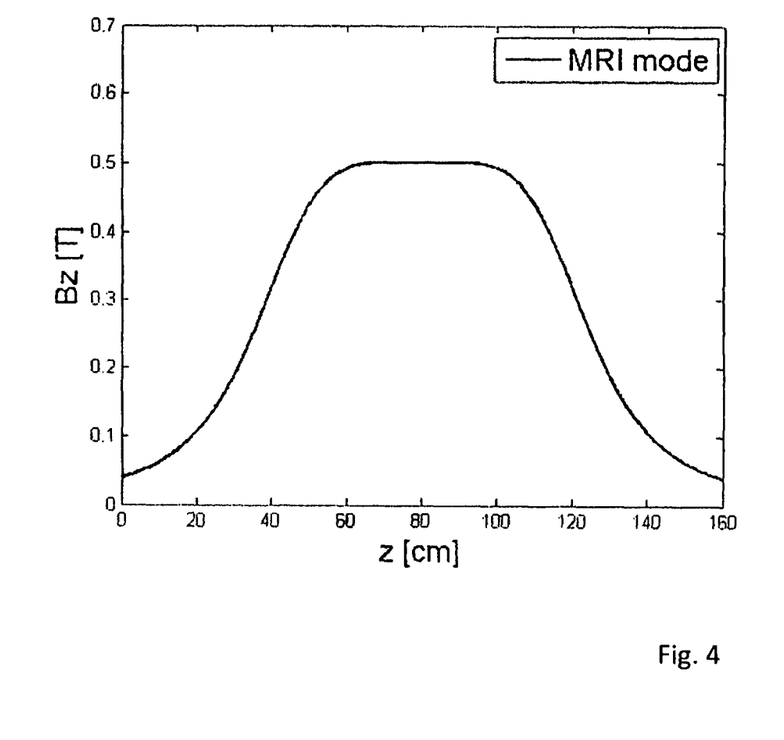
FIG. 4 shows an axial field profile of the main magnet coil system along the z axis (at r=0 cm) in the MRI mode (polarization field profile).
Figure 5:
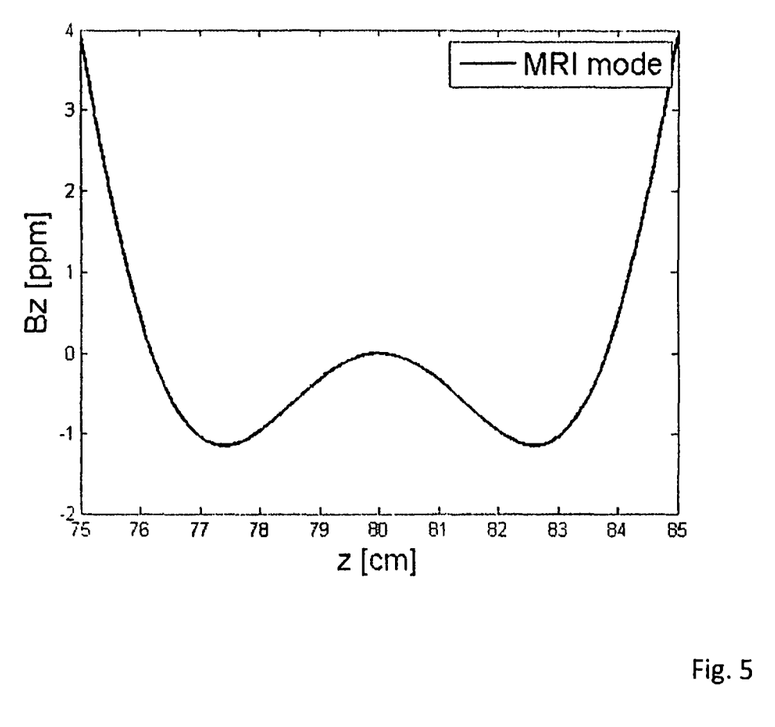
FIG. 5 shows an axial field profile of the main magnet coil system along the z axis (at r=0 cm) in the area of the MRI volume under investigation 162 in the MRI mode (polarization field profile).
Figure 6:
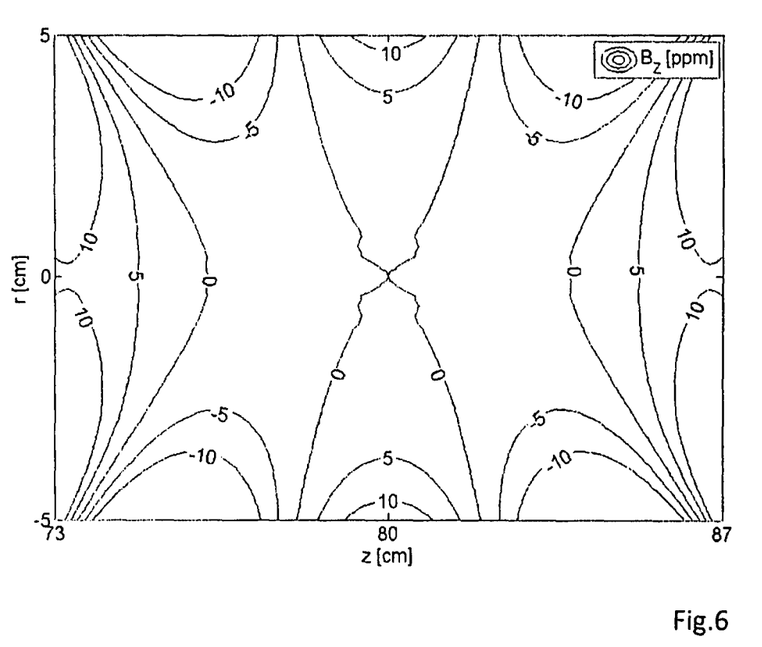
FIG. 6 shows a homogeneity plot of the polarization field in the area of the MRI volume under investigation 162.
Figure 8:
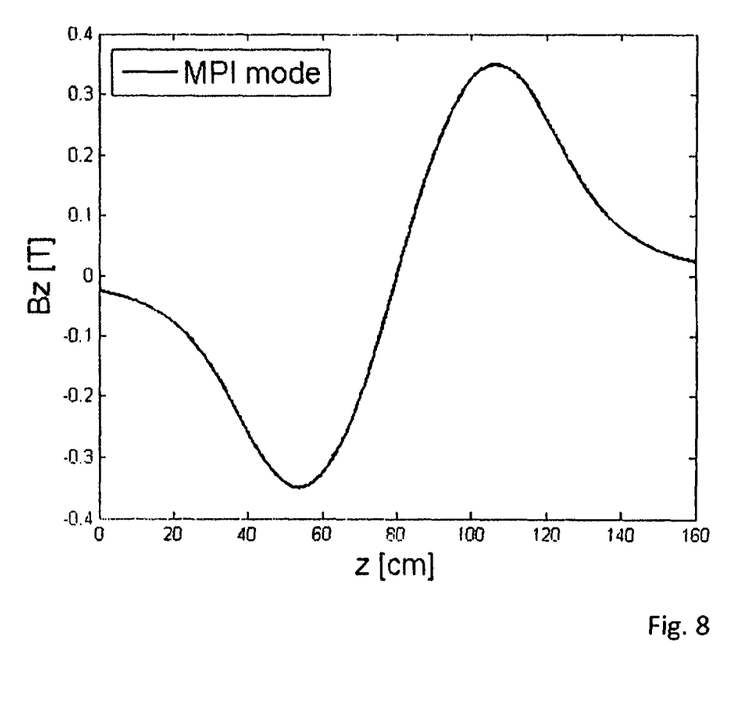
FIG. 8 shows an axial field profile of the main magnet coil system along the z axis (at r=0 cm) in the MPI mode (selection field profile).
Figure 9:
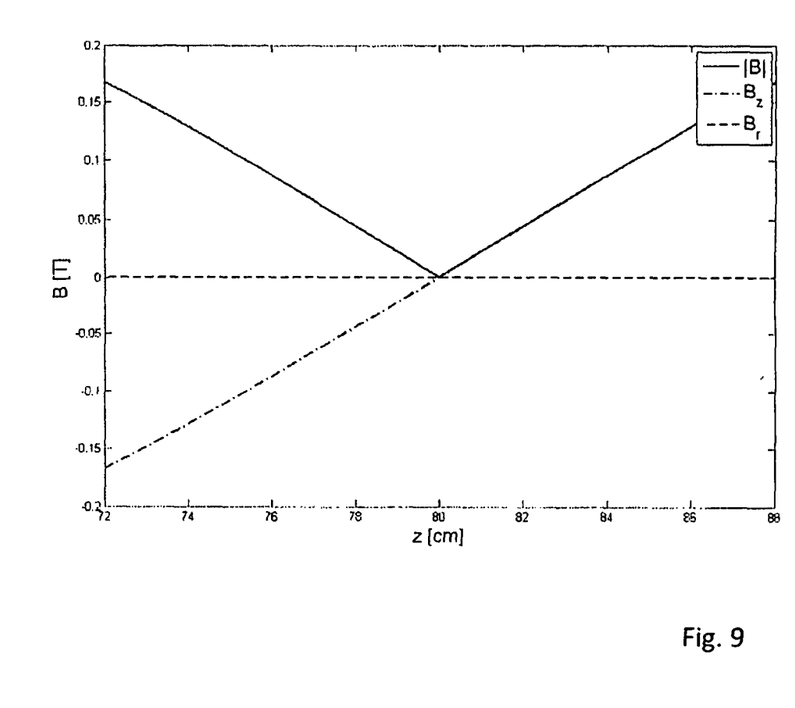
FIG. 9 shows an axial field profile of the main magnet coil system along the z axis (at r=0 cm) in the area of the MPI volume under investigation 161 or the field-free point in the MPI mode (selection field profile).
Figure 10:
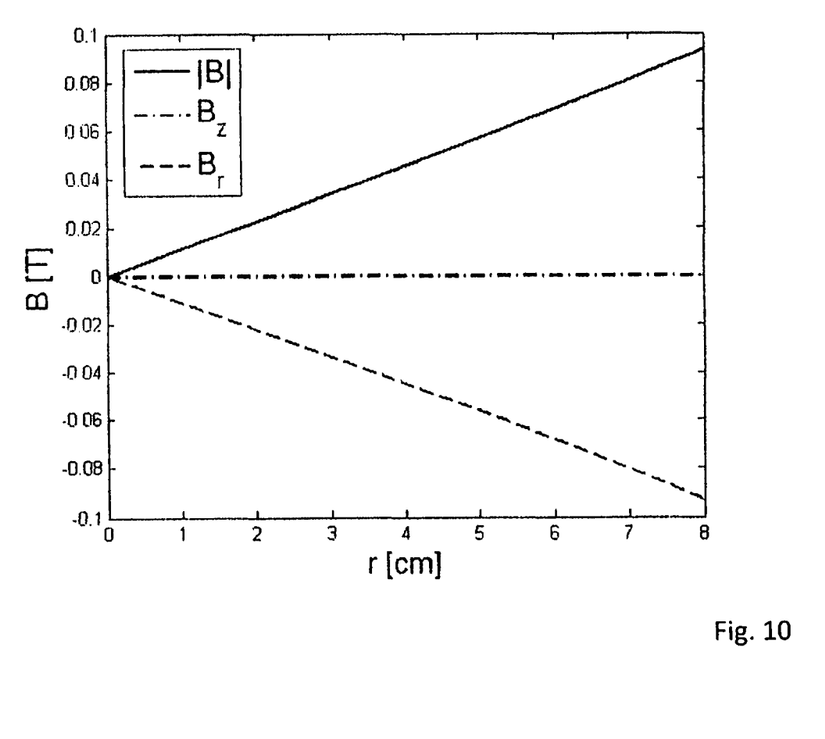
FIG. 10 shows a radial field profile of the main magnet coil system at z=80 cm in the area of the MPI volume under investigation 161 or the field-free point in the MPI mode (selection field profile).

With a direct current of 500 A, held stable to ppm, of a linearly controlled power supply unit 180, one obtains in the MRI mode partial coil system, with a (100a1, 100a2) and b (100b1, 100b2) having the same polarity and connected in series (cf. FIG. 1), a magnetic field (polarization field) of 6th order of a strength of 0.5 T (cf. FIGS. 4, 5, 6). The MPI mode, with partial coil system a (100a1, 100a2) and b (100b1, 100b2) having opposite polarity and connected in series (cf. FIG. 2), has a magnetic field gradient (selection field) of 2.2 T/m in the z direction including a field-free point (cf. FIGS. 8, 9, 10) which represents the center of the volume of investigation (161).

The reversal of polarity of a partial coil system, in the present embodiment the partial coil system 100a1 and 100a2, and therefore the modality change, are effected via a polarity reversal device 190 installed in the power supply unit 180 for the main magnet coil system. This configuration of the polarity reversal device 190 within the power supply unit 180 ensures safe reversal of polarity since inversion of the current flow direction of the partial coil system a (100a1 and 100a2) is permitted only when the magnetic field has been eliminated (current strength=0 A).

For increasing the field homogeneity in the MRI mode, a resistive electromagnetic coil system is integrated, which is used as a shim coil system 110 of second order with the following shim values:
$G_{Z^2}=0.053$ T/m$^2$/A, $G_{XZ}=G_{YZ}=0.018$ T/m$^2$/A, $G_{X^2-Y^2}=G_{XY}=0.012$ T/m$^2$/A.

An actively shielded MRI gradient coil system 130 with the following values is used for spatially encoding in the MRI mode and as a shim coil system of first order:
$G_X=8$ µT/cm/A, $G_Y=9.7$ µT/cm/A, $G_Z=8.5$ µT/cm/A.

Due to the RF strand design and with active electrically non-conductive cooling or electrically minimally conductive cooling (plastic cooling channels, coolant: demineralized water), this MRI gradient coil system has a quick switching behavior and therefore exact gradient trajectories and is moreover transparent to LF radiation of the drive field coil system 140. This transparency to LF radiation of the MRI gradient system minimizes the eddy currents induced in the MPI mode by the drive field in the surrounding conductive structures, which therefore minimizes attenuation/damping of the drive field.

The embodiment moreover includes an MRI RF transmission-receiver coil (Tx/Rx) 150 which is adjusted to the Larmor frequency of 0.5 T. The MRI-RF coil 150 being the innermost element (i.e. within the drive field coil opening (cf. FIGS. 1 and 2) is maximally close to the object under investigation 170 in order to maximize the sensitivity of this MRI-RF coil 150.

Figure 7:
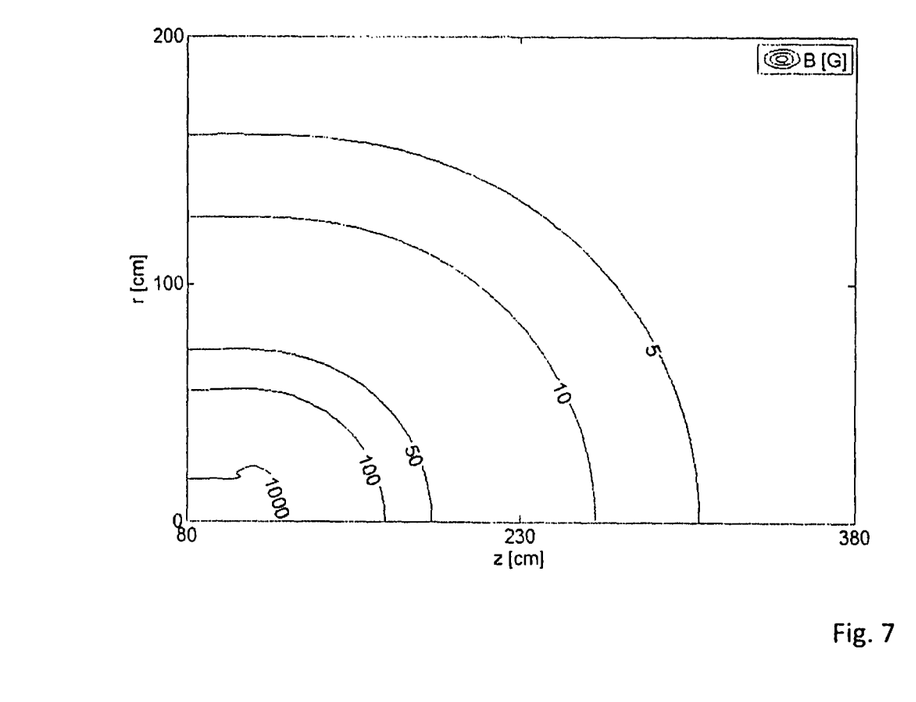
FIG. 7 shows a stray field plot of the polarization field.

The stray field plot of the device in the MRI mode (polarization field) is illustrated in FIG. 7.

The resistive drive field coil system 140 is used as LF transmission receiver coil (Tx/Rx) in the MPI mode, with the following field values:
Bx=0.095 mT/A, By=0.085 mT/A, Bz=0.133 mT/A.

This coil system is also realized from an RF strand and with an active, electrically non-conductive cooling means (glass fiber reinforced cooling channels, cooling medium: transformer oil).

The design with RF strand minimizes the line losses for high-frequency currents in comparison with solid wire, since the cross-section for high-frequency currents, which is effectively involved in the current flow, is maximized in the RF strand (skin effect, proximity effect).

The design of the cooling system within the drive field coil system 140 with electrically non-conductive glass fiber reinforced cooling channels minimizes eddy currents in these structures.

Figure 3:
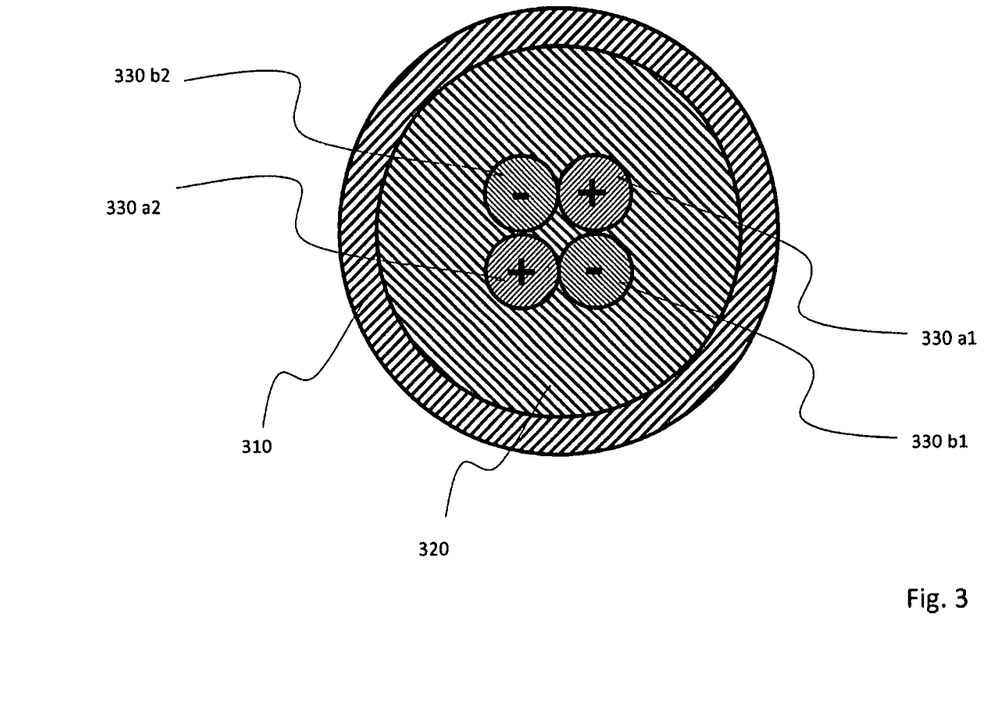
FIG. 3 shows a schematic sectional view of an electrical connection of the drive field coil system for a drive field channel. The RF strands 330a1, 330a2, 330b1, 330b2 are guided as twisted quadrupole within a feed or discharge line 310 filled with coolant 320 of the drive field coil system.

The electrical connections 330*a*1-2, 330*b*1-2 of the MPI drive field coil system are guided as a twisted quadrupole (cf. FIG. 3), which minimizes coupling and sensitivity to disturbance signals of the individual MPI drive field channels. The electrical connections of the MPI drive field coil system are moreover already actively cooled by the guidance of the quadrupole configurations within the feed or discharge lines 310 for the cooling medium 320 and can therefore be minimized in view of the line cross-section that is used.

Figure 11:
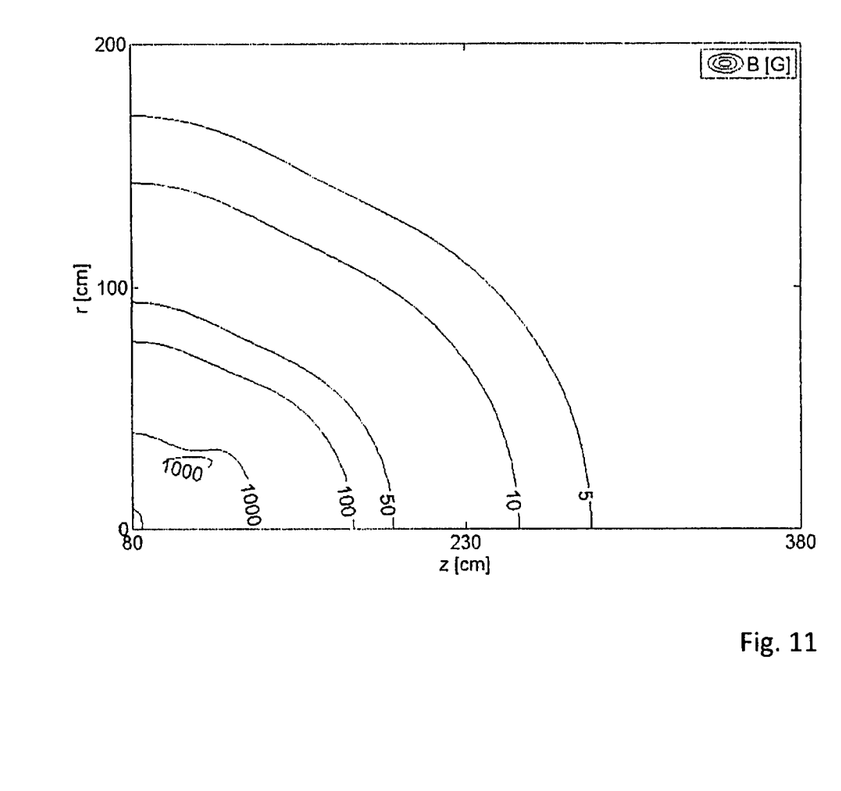
FIG. 11 shows a stray field plot of the selection field.

The drive field coil system is passively shielded by means of a copper tube 110 of a diameter of 300 mm. The stray field plot of the device in the MPI mode (selection field) is illustrated in FIG. 11.

All field-generating elements (the main magnet coil system 100*a*1-2, 100*b*1-2, the shim coil system 110, the MRI gradient coil system 130 and the drive field coil system 140) are concentrically arranged and for this reason, the magnetic centers of these components and therefore also the centers of the two volumes under investigation 161, 162 have the same spatial point.

The properties of this device permit alternating investigation of the measurement object 170 by means of MPI and MRI, wherein the modality change can be performed without relocation of the object under investigation 170 by means of inverting the current flow of a partial coil element 100*a*1 and 100*a*2 or 100*b*1 and 100*b*2.

LIST OF REFERENCE NUMERALS

100*a*1, 100*a*2 partial coil system a
100*b*1, 100*b*2 partial coil system b
110 shim coil system
120 passive shielding element, copper tube
130 MRI gradient coil system
140 MPI drive field coil system (Tx/Rx)
150 MRI RF transmission-receiver coil (Tx/Rx)
161 MPI volume under investigation
162 MRI volume under investigation
170 measurement object
180 linearly controlled power supply unit for the main magnet coil system
190 polarity reversal device
310 feed or discharge lines of the cooling medium for the MPI drive field coil system
320 cooling medium
330*a*1-2, 330*b*1-2 electrical connection of a drive field coil

REFERENCES

[1] Gleich B and Weizenecker J 2005 Tomographic imaging using the nonlinear response of magnetic particles Nature 435 1214-7
[2] Sattel T F, Knopp T, Biederer S, Gleich B, Weizenecker J, Borgert J and Buzug T M 2009 Single-sided device for magnetic particle imaging, J. Phys. D: Appl. Phys. 42 1-5
[3] Weizenecker J, Gleich B, Rahmer J, Dahnke H and Borgert J 2009 Three-dimensional real-time in vivo magnetic particle imaging. Phys. Med. Biol. 54 L1-L10
[4] Weizenecker J, Borgert J and Gleich B 2007 A simulation study on the resolution and sensitivity of magnetic particle imaging. Phys. Med. Biol. 52 6363-74
[5] Knopp T, Biederer S, Sattel T, Weizenecker J, Gleich B, Borgert J and Buzug T M 2009 Trajectory analysis for magnetic particle imaging. Phys. Med. Biol. 54 385-97
[6] Vlaadingerbroek M T and den Boer J A 2003 Magnetic resonance Imaging, Springer-Verlag 3rd Edition
[7] Magnetic Particle Imaging—A Novel SPIO Nanoparticle Imaging Technique. Springer Springer Proceedings in Physics

We claim:

1. A device for alternating examination of a measurement object by means of MPI (magnetic particle imaging) and by means of MRI (magnetic resonance imaging), the device comprising:
a resistive drive field coil system for generating a drive field, said resistive drive field coil system having electrical feed lines;
a resistive MRI gradient coil system;
a main magnet coil system disposed around a z axis, said main magnet coil system having two coaxial partial coil systems that are arranged mirror-symmetrically with respect to a central plane running perpendicularly to the z axis through a first volume under investigation, said main magnet coil system generating a homogeneous field of at least 0.5 T and of at least 6th order for MRI operation within said first volume under investigation and a spatially strongly varying magnetic field profile for MPI operation within a second volume under investigation, wherein said first and said second volumes under investigation at least partially overlap, said spatially strongly varying magnetic field profile having field vectors which are different with respect to direction or magnitude at all spatial points and having a field magnitude zero at one spatial point;
a device for reversing a polarity of current through one of said partial coil systems, wherein said main magnet coil system is designed in such a fashion that it generates said homogeneous magnetic field in said first volume under investigation when polarities of said partial coil systems are the same and said spatially strongly varying magnetic field profile in said second volume under investigation when said polarities are opposite; and
a linearly controlled power supply, said linearly controlled power supply supplying a direct current to said partial coil systems, wherein said direct current is held stable to ppm during MRI operation.

2. The device of claim 1, wherein said main magnet coil system is designed as a resistive electromagnetic coil system.

3. The device of claim 1, wherein said main magnet coil system is optimized in view of minimum power loss for a specific field strength by means of a dispersed current density distribution.

4. The device of claim 1, wherein at least one of said partial coil systems is designed as a solenoid coil or a configuration of solenoid-shaped components.

5. The device of claim 1, wherein said device for reversing the polarity of the current through one of said partial coil systems is integrated in said linearly controlled power supply for said main magnet coil system.

6. The device of claim 1, wherein said resistive drive field coil system is produced from an RF (radio frequency) strand.

7. The device of claim 1, wherein said electrical feed lines of said resistive drive field coil system are designed as quadrupoles.

8. The device of claim 1, wherein said resistive drive field coil system has a first active cooling system that circulates an electrically non-conductive coolant within said drive field coil system in electrically non-conductive channels of said first cooling system.

9. The device of claim 8, wherein said electrical feed lines of said resistive drive field coil system are laid within feed or discharge lines for coolant of said first cooling system.

10. The device of claim 1, wherein said MRI gradient coil system is produced from an RF (radio frequency) strand.

11. The device of claim 1, wherein said MRI gradient coil system has a second active cooling system that circulates an electrically non-conductive coolant within the MRI gradient coil system in electrically non-conductive channels of said second cooling system.

12. The device of claim 1, wherein said MRI gradient coil system is actively or passively shielded.

13. The device of claim 1, wherein all field-generating elements for MRI and MPI have a same magnetic center.

* * * * *

UNITED STATES PATENT AND TRADEMARK OFFICE
CERTIFICATE OF CORRECTION

| | |
|---|---|
| PATENT NO. | : 10,191,130 B2 |
| APPLICATION NO. | : 14/647452 |
| DATED | : January 29, 2019 |
| INVENTOR(S) | : Heidenreich et al. |

Page 1 of 1

It is certified that error appears in the above-identified patent and that said Letters Patent is hereby corrected as shown below:

On the Title Page

Item (56), Column 2, Line 1, U.S. patent document should read as follows:
2003/0085703 A1 5/2003 Gleich Signed and Sealed this
Twenty-fifth Day of June, 2019

Andrei Iancu
*Director of the United States Patent and Trademark Office*